(12) United States Patent
Bozinov et al.

(10) Patent No.: US 7,031,844 B2
(45) Date of Patent: Apr. 18, 2006

(54) CLUSTER ANALYSIS OF GENETIC MICROARRAY IMAGES

(75) Inventors: Daniel Bozinov, Omaha, NE (US); Jörg Rahnenführer, Omaha, NE (US)

(73) Assignee: The Board of Regents of the University of Nebraska, Omaha, NE (US)

( * ) Notice: Subject to any disclaimer, the term of this patent is extended or adjusted under 35 U.S.C. 154(b) by 250 days.

(21) Appl. No.: 10/100,262

(22) Filed: Mar. 18, 2002

(65) Prior Publication Data

US 2003/0175720 A1 Sep. 18, 2003

(51) Int. Cl.
G06K 9/00 (2006.01)
G01N 33/48 (2006.01)
G06F 7/00 (2006.01)

(52) U.S. Cl. .............................. 702/19; 702/20; 435/6; 707/102; 382/129; 382/130

(58) Field of Classification Search ............ 702/19–29; 707/102; 703/11; 435/6
See application file for complete search history.

(56) References Cited

U.S. PATENT DOCUMENTS

| | | | |
|---|---|---|---|
| 6,141,096 A | 10/2000 | Stern et al. | |
| 6,245,517 B1 | 6/2001 | Chen et al. | |
| 6,251,601 B1 | 6/2001 | Bao et al. | |
| 6,252,236 B1* | 6/2001 | Trulson et al. ............ | 250/458.1 |
| 6,587,585 B1* | 7/2003 | Wesolkowski et al. ..... | 382/172 |
| 2003/0009467 A1* | 1/2003 | Perrizo ....................... | 707/100 |
| 2003/0065632 A1* | 4/2003 | Hubey ......................... | 706/15 |
| 2003/0186279 A1* | 10/2003 | Kennedy et al. ............... | 435/6 |
| 2003/0186280 A1* | 10/2003 | Kennedy ....................... | 435/6 |
| 2003/0208488 A1* | 11/2003 | Perrizo ......................... | 707/6 |

OTHER PUBLICATIONS

Yeung, K-Y. Practical Approach to Microarray Data Analysis (2003), 274-288. Editor(s): Berrar, Daniel P.; Dubitzky, Werner; Granzow, Martin. Publisher: Kluwer Academic Publishers, Norwell, Mass.*

Chen, Y. et al. "Ratio-Based Decisions and the Quantitative Analysis of cDNA Microarray Images"; Journal of Biomedical Optics, 2(4): 364-374 (1997).

Duggan, D.J. et al. "Expression profiling using cDNA microarrays"; Nature Genetics Supplement, 21: 10-14 (1999).

Eisen, M.B. et al. "Cluster analysis and display of genome-wide expression patterns"; Proc. Natl. Acad. Sci. USA, 95: 14863-14868 (1998).

(Continued)

Primary Examiner—Mary K. Zeman
(74) Attorney, Agent, or Firm—Dann Dorfman Herrell and Skillman; Kathleen D. Rigaut (57) ABSTRACT

A method for determining relative incidence of a binding substance within two biological samples is provided. The two samples are labeled with luminescent materials having different chromatic properties. An image of the luminescent materials upon a binding site of a microarray is analyzed as two clusters of data points scattered about respective representative pairs of chromatic intensity values. The relative incidence of the binding substance is determined as a ratio of differences between corresponding indices of the representative pairs.

6 Claims, 4 Drawing Sheets

OTHER PUBLICATIONS

Golub, T.R. et al. "Molecular Classification of Cancer: Class Discovery and Class Prediction by Gene Expression Monitoring"; Science, 286: 531-537 (1999).

Potzelberger, K. et al. "Clustering and Quantization by MSP-Partitions"; to appear in: Statistics and Decisions pp. 1-40.

Rahnenfuhrer, J. "Multivariate permutation tests for the k-sample problem with clustered data"; to appear in: Computational Statistics, Feb. 2002, pp. 1-20.

Ross, D.T. et al. "Systematic variation in gene expression patterns in human cancer cell lines"; Nature Genetics, 24: 227-235 (2000).

Schena, M. et al. "Quantitative Monitoring of Gene Expression Patterns with a Complimentary DNA Microarray"; Science, 210: 467-470 (1995).

Shalon, D. et al. "A DNA Microarray System for Analyzing Complex DNA Samples Using Two-color Fluorescent Probe Hybridization"; Genome Research, 6: 639-645 (1996).

Strasser, H. Reduction of complexity, Technical report, Department of Statistics, Vienna University of Economics and Business Administration, pp. 1-36 (2000).

Kaufman, L. & Rousseeuw, P.J. *Finding Groups in data: An introduction to cluster analysis*, "Partitioning Around Medoids (Program PAM)" Chapter 2, pp. 68-108: (1990).

* cited by examiner

ID
CLUSTER ANALYSIS OF GENETIC MICROARRAY IMAGES

FIELD OF THE INVENTION

The present invention relates to an analysis technique for use in differential gene expression studies employing DNA microarrays. In particular, the present invention relates to the use of a clustering analysis method for determining the differential expression levels of targeted nucleic acid molecules based on relative intensities and intensity ratios of a plurality of detectably labeled hybridizing nucleic acid sequences. The methods of the present invention are also applicable to the analysis of DNA-protein, RNA-protein, and protein-protein interactions.

BACKGROUND

DNA microarrays are known in which genetic probes are affixed to a substrate at discrete locations for binding with a sample containing labeled genetic material. Terminologies that have been used in the literature to describe this technology include, biochip, DNA chip, DNA microarray and gene array. DNA microarrays are fabricated by high-speed robotics, generally on glass but sometimes on nylon substrates, for which probes with known identity are used to determine complementary binding, thus allowing massively parallel gene expression studies.

In one type of study employing DNA microarrays, the genetic composition of two samples is compared. A first sample, which may be a control sample having a known genetic composition, is labeled with a first detectable label such as red-fluorescent dye, Cy5. A second sample is labeled with a second detectable label such as green-fluorescent dye, Cy3. While Cy3 and Cy5 are exemplified, one of skill in the art is aware that a variety of different detectable labels are commercially available. The two samples are then mixed and applied to the microarray for hybridization with any complementary probes thereon. In the case of samples containing mRNA, for example, the microarray is provided to have a suitable set of cDNA spots for binding. After hybridization, images of the microarray are obtained using a laser scanner at wavelengths of 635 nm (red) and 532 nm (green). In the resulting image, differences between the composition of the two samples is indicated by the respective red and green intensities of the probe locations on the microarray, while the relative abundance of any particular mRNA sequence within the two samples is indicated by the red/green intensity ratio of each spot.

Due to the large number of probes which may be present on the microarray, it is desirable to apply an automated image analysis technique to the determination of red and green intensities present on the array, and the red/green ratio for each spot. Traditional methods of performing this analysis have been accomplished by obtaining a digital image of the chip under fluorescent excitation, and then performing steps of addressing, segmentation, and reduction. In the addressing step, the image areas of the array are located. For example, using the known geometry of the array, the intensity data from portions of the array image corresponding to the probe locations are obtained. Then, for each probe location, the image portion is segmented into background and foreground intensity values by a thresholding function. Finally, in the reduction step, a scalar value of red intensity and green intensity is obtained, from which a value of red/green ratio is calculated.

Early automated analysis methods based on the sequence of steps described above were predicated on the assumption that each excited probe location would be a circular region corresponding the presumed probe location, and that background and foreground intensities would be constant across the array. In practice, however, significant variations in background illumination and spot size and shape occur, which adversely influences the results which can be obtained by methods based on an ideal assumption. Variations occurring in practice include spots of variable size; variable contour, in which the spots have semicircular, toroidal, oval, or other unanticipated shapes; variable background intensities; and spatial artifacts such as smeared or incorrectly segmented probe locations.

Several methods have been developed to overcome analysis difficulties presented by non-uniformities of images of hybridized samples on DNA microarrays. Adaptive shape segmentation techniques are known in which an initial starting point in the image is chosen and then enlarged in the neighborhood of the starting point until a statistical criterion indicative of spot detection has been reached. In a second set of techniques, a histogram of pixel intensity values is produced, and then the respective background and foreground pixels are determined based upon respective percentile ranges of pixels falling within the lower and upper distributions of the histogram. These methods are susceptible to erroneous results from the presence of a relatively few anomalous values within the image of each spot area.

It would be desirable to provide a method of automated DNA microarray analysis which is more accurate and less sensitive to variations of intensity and shape among the probe locations of a digitized fluorescence image of a DNA microarray.

SUMMARY OF THE INVENTION

In accordance with the present invention, a clustering algorithm is employed in the analysis of digitized fluorescence images of DNA microarrays. For each pixel $x_i$ in a gene spot image, the red and green intensity values are determined as a vector $(R_i, G_i)$. While Cy5 (red) and Cy3 (green) are exemplified, a variety of different detectable labels are commercially available and may be used in conjunction with the clustering algorithm of the present invention. The set of (R,G) values for each spot is then analyzed as a set of two clusters, and the medoid of each cluster is determined by minimization of an objective function. The two medoids represent a background medoid ($R_{bg}$, $G_{bg}$) and a foreground medoid ($R_{fg}$, $G_{fg}$). The red/green intensity ratio for each spot is then computed as the ratio $$R/G=(R_{fg}-R_{bg})/(G_{fg}-G_{bg}).$$

This expression corresponds to the shape of a line connecting the medoids in R-G space. Two such clustering algorithms are provided. In the first clustering algorithm, a PAM (Partitioning Around Medoids) method is applied to the image data from each gene spot in order to determine the R and G intensity values for the foreground and background medoids. In the second clustering algorithm, a K-means method is applied. Both of these methods provide superior results compared to prior segmentation and reduction methods, with varying levels of computational complexity required.

BRIEF DESCRIPTION OF THE DRAWINGS

The foregoing summary, as well as the following detailed description will be best understood in conjunction with the attached drawings in which.

DETAILED DESCRIPTION

The following description sets forth the general procedures involved in practicing the present invention. To the extent that specific materials are mentioned, it is merely for purposes of illustration and is not intended to limit the invention. Unless otherwise specified, general hybridization procedures, such as those set forth in Current Protocols in Molecular Biology, Ausubel et al. eds., J W Wiley and Sons, NY (1998) and Molecular Cloning A Laboratory Manual, Second Edition, Sambrook et al. eds., Cold Spring Harbor Laboratory Press, 1989 are utilized.

Definitions

Various terms relating to the biological molecules of the present invention are used hereinabove and also throughout the specifications and claims.

"Nucleic acid" or a "nucleic acid molecule" as used herein refers to any DNA or RNA molecule, either single or double stranded and, if single stranded, the molecule of its complementary sequence in either linear or circular form. In discussing nucleic acid molecules, a sequence or structure of a particular nucleic acid molecule may be described herein according to the normal convention of providing the sequence in the 5' to 3' direction. With reference to nucleic acids of the invention, the term "isolated nucleic acid" is sometimes used. This term, when applied to DNA, refers to a DNA molecule that is separated from sequences with which it is immediately contiguous in the naturally occurring genome of the organism in which it originated. For example, an "isolated nucleic acid" may comprise a DNA molecule inserted into a vector, such as a plasmid or virus vector, or integrated into the genomic DNA of a prokaryotic or eukaryotic cell or host organism.

When applied to RNA, the term "isolated nucleic acid" refers primarily to an RNA molecule encoded by an isolated DNA molecule as defined above. Alternatively, the term may refer to an RNA molecule that has been sufficiently separated from other nucleic acids with which it would be associated in its natural state (i.e., in cells or tissues). An isolated nucleic acid (either DNA or RNA) may further represent a molecule produced directly by biological or synthetic means and separated from other components present during its production.

The term "isolated protein" or "isolated and purified protein" refers primarily to a protein or polypeptide that has been sufficiently separated from other proteins with which it would naturally be associated, so as to exist in "substantially pure" form. "Isolated" is not meant to exclude artificial or synthetic mixtures with other compounds or materials, or the presence of impurities that do not interfere with the fundamental activity, and that may be present, for example, due to incomplete purification, addition of stabilizers, or compounding into, for example, pharmaceutically acceptable preparations.

A "fragment" or "portion" of a protein or polypeptide means a stretch of amino acid residues of at least about five to seven contiguous amino acids, often at least about seven to nine contiguous amino acids, typically at least about nine to thirteen contiguous amino acids and, most preferably, at least about twenty to thirty or more contiguous amino acids.

The phrase "consisting essentially of" when referring to a particular nucleotide or amino acid means a sequence having the properties of a given SEQ ID NO:. For example, when used in reference to a nucleic acid sequence, the phrase includes the sequence per se and molecular modifications that would not affect the basic and novel functional characteristics of the sequence.

The term "probe" as used herein refers to an oligonucleotide; polynucleotide or nucleic acid, either RNA or DNA, whether occurring naturally as in a purified restriction enzyme digest or produced synthetically, which is capable of annealing with or specifically hybridizing to a nucleic acid with sequences complementary to the probe. A probe may be either single-stranded or double-stranded. The exact length of the probe will depend upon many factors, including temperature, source of probe and the method used. For example, for diagnostic applications, depending on the complexity of the target sequence, the oligonucleotide probe typically contains 15–25 or more nucleotides, although it may contain fewer nucleotides. The probes herein are selected to be "substantially" complementary to different strands of a particular target nucleic acid sequence. Such probes must, therefore, be sufficiently complementary so as to be able to "specifically hybridize" or anneal with their respective target strands under a set of pre-determined conditions. Therefore, the probe sequence need not reflect the exact complementary sequence of the target. For example, a non-complementary nucleotide fragment may be attached to the 5' or 3' end of the probe, with the remainder of the probe sequence being complementary to the target strand. Alternatively, non-complementary bases or longer sequences can be interspersed into the probe, provided that the probe sequence has sufficient complementarity with the sequence of the target nucleic acid to anneal therewith specifically.

The term "specifically hybridize" refers to the association between two single-stranded nucleic acid molecules of sufficiently complementary sequence to permit such hybridization under pre-determined conditions generally used in the art (sometimes termed "substantially complementary"). In particular, the term refers to hybridization of an oligonucleotide with a substantially complementary sequence contained within a single-stranded DNA or RNA molecule of the invention, to the substantial exclusion of hybridization of the oligonucleotide with single-stranded nucleic acids of non-complementary sequence.

A "specific binding pair" comprises a specific binding member (sbm) and a binding partner (bp) which have a particular specificity for each other and which in normal conditions bind to each other in preference to other molecules. Examples of specific binding pairs are nucleotide sequences and nucleotide sequence-binding proteins, antigens and antibodies, ligands and receptors and complementary nucleotide sequences. The skilled person is aware of many other examples and they do not need to be listed here. Further, the term "specific binding pair" is also applicable where either or both of the specific binding member and the binding partner comprise a part of a large molecule. In embodiments in which the specific binding pair are nucleic acid sequences, they will be of a length to hybridize to each other under conditions of the assay, preferably greater than 10 nucleotides long, more preferably greater than 15 or 20 nucleotides long.

The term "substantially pure" refers to a preparation comprising at least 50–60% by weight of a given material (e.g., nucleic acid, oligonucleotide, polypeptide etc.). More preferably, the preparation comprises at least 75% by weight, and most preferably 90–95% by weight of the given compound. Purity is measured by methods appropriate for the given compound (e.g. chromatographic methods, agarose or polyacrylamide gel electrophoresis, HPLC analysis, and the like).

The term "tag," "tag sequence" or "protein tag" refers to a chemical moiety, either a nucleotide, oligonucleotide, polynucleotide or an amino acid, peptide or protein or other chemical, that when added to another sequence, provides additional utility or confers useful properties, particularly in the detection or isolation, to that sequence. Thus, for example, a homopolymer nucleic acid sequence or a nucleic acid sequence complementary to a capture oligonucleotide may be added to a primer or probe sequence to facilitate the subsequent isolation of an extension product or hybridized product. Chemical tag moieties include such molecules as biotin, which may be added to either nucleic acids or proteins and facilitate isolation or detection by interaction with avidin reagents, and the like. Numerous tag moieties are known to, and can be envisioned by, the trained artisan, and are contemplated to be within the scope of this definition.

Nucleic Acid Molecules and Polypeptides

Nucleic acid molecules may be prepared by two general methods: (1) they may be synthesized from appropriate nucleotide triphosphates, or (2) they may be isolated from biological sources. Both methods utilize protocols well known in the art.

In some circumstances wherein a specifically targeted or directed comparison is desired, the availability of nucleotide sequence information, such as that derived from databases comprised of Expressed Sequence Tags (ESTs), cDNA libraries, and genomic libraries enables preparation of an isolated nucleic acid molecule of the invention by oligonucleotide synthesis. Synthetic oligonucleotides may be prepared by the phosphoramadite method employed in the Applied Biosystems 38A DNA Synthesizer or similar devices. The resultant oligonucleotide may be purified according to methods known in the art, such as high performance liquid chromatography (HPLC). Oligonucleotides or synthetic DNA molecules so generated may then be used as probes or competitors in the methods of the present invention.

In accordance with the present invention, hybridization and washing conditions of appropriate stringency for a particular application may be established. For example, hybridizations may be performed, according to the method of Sambrook et al., (supra) using a hybridization solution comprising: 5×SSC, 5× Denhardt's reagent, 0.5–1.0% SDS, 100 µg/ml denatured, fragmented salmon sperm DNA, 0.05% sodium pyrophosphate and up to 50% formamide. Hybridization is carried out at 37–42° C. for at least six hours. Following hybridization, filters are washed as follows: (1) 5 minutes at room temperature in 2×SSC and 0.5–1% SDS; (2) 15 minutes at room temperature in 2×SSC and 0.1% SDS; (3) 30 minutes–1 hour at 37° C. in 1×SSC and 1% SDS; (4) 2 hours at 42–65° C. in 1×SSC and 1% SDS, changing the solution every 30 minutes.

One common formula for calculating the stringency conditions required to achieve hybridization between nucleic acid molecules of a specified sequence homology is (Sambrook et al., 1989):

$$T_m = 81.5° \text{ C.} + 16.6 \text{Log}[\text{Na+}] + 0.41(\% \, G+C) - 0.63(\% \text{ formamide}) - 600/\#bp \text{ in duplex}$$

As an illustration of the above formula, using [Na+]=[0.368] and 50% formamide, with GC content of 42% and an average probe size of 200 bases, the $T_m$ is 57° C. The $T_m$ of a DNA duplex decreases by 1–1.5° C. with every 1% decrease in homology. Thus, targets with greater than about 75% sequence identity would be observed using a hybridization temperature of 42° C. Such a sequence would be considered substantially homologous to the nucleic acid sequence of the present invention.

Nucleic acid molecules of the invention include cDNA, genomic DNA, RNA, and fragments thereof which may be single- or double-stranded. Thus, this invention provides oligonucleotides (sense or antisense strands of DNA or RNA) having sequences capable of hybridizing with at least one sequence of a nucleic acid molecule of the present invention, such as selected segments one of the nucleic acid sequences immobilized on a microarray.

The present invention also provides for analysis of interactions between a specific binding pair, wherein a specific binding member (sbm) is a nucleic acid molecule (e.g., cDNA, genomic DNA, RNA, and fragments thereof which may be single- or double-stranded) and wherein a binding partner (bp) is a polypeptide.

The present invention also provides for analysis of interactions between a specific binding pair, wherein both the sbm and the bp are polypeptide molecules (e.g., full length proteins and fragments thereof). One of skill in the art would appreciate that such polypeptide molecules may be generated by a variety of protocols (e.g., recombinantly expressed, synthesized, or isolated in native form by affinity purification). Such protocols are well known and described in a variety of laboratory manuals, including, for example, Sambrook et al. (supra) and Ausubel et al. (supra).

Polypeptide molecules may be prepared in a variety of ways, according to known methods. The polypeptide or protein molecules may be purified from appropriate sources, e.g., human or animal cultured cells or tissues, by immunoaffinity purification. However, this is not a preferred method due to the small amounts of protein likely to be present in a given cell type at any time.

The availability of nucleic acid molecules encoding polypeptides enables production of the encoded proteins using in vitro expression methods known in the art. For example, a cDNA or gene may be cloned into an appropriate in vitro transcription vector, such a pSP64 or pSP65 for in vitro transcription, followed by cell-free translation in a suitable cell-free translation system, such as wheat germ or rabbit reticulocytes. In vitro transcription and translation systems are commercially available, e.g., from Promega Biotech, Madison, Wis. or BRL, Rockville, Md.

Alternatively, in a preferred embodiment, larger quantities of a polypeptide or a plurality of polypeptides may be produced by expression in a suitable prokaryotic or eukaryotic system. For example, part or all of a DNA molecule, such as a cDNA, may be inserted into a plasmid vector adapted for expression in a bacterial cell, such as E. coli, or into a baculovirus vector for expression in an insect cell. Such vectors comprise the regulatory elements necessary for expression of the DNA in the host cell, positioned in such a manner as to permit expression of the DNA in the host cell. Such regulatory elements required for expression include promoter sequences, transcription initiation sequences and, optionally, enhancer sequences.

The polypeptide(s) produced by gene expression in a recombinant prokaryotic or eukaryotic system may be purified according to methods known in the art. In a preferred embodiment, a commercially available expression/secretion system may be used, whereby the recombinant protein(s) are expressed and thereafter secreted from the host cell, to be easily purified from the surrounding medium. If expression/secretion vectors are not used, an alternative approach involves purifying the recombinant protein by affinity separation, such as by immunological interaction with antibodies that bind specifically to the recombinant protein. Such methods are commonly used by skilled practitioners.

Polypeptides prepared by the aforementioned methods, may be analyzed according to standard procedures. For example, such proteins may be subjected to amino acid sequence analysis, according to known methods.

Labeling Methods/Strategies

In a preferred embodiment, the interaction of specific binding pairs (e.g., nucleic acid complexes, nucleic acid-protein complexes, or protein-protein complexes) are detected by assessing one or more labels attached to the sample nucleic acids, polypeptides, or probes. In a particularly preferred embodiment, the interaction of hybridized nucleic acids are detected by assessing one or more labels attached to the sample nucleic acids or probes. The labels may be incorporated by any of a number of means well known to those of skill in the art. However, in a preferred embodiment, the label is simultaneously incorporated during the amplification step in the preparation of the sample nucleic acids or probes. For example, polymerase chain reaction (PCR) with labeled primers or labeled nucleotides will provide a labeled amplification product. The nucleic acid (e.g., DNA) may be amplified, for example, in the presence of labeled deoxynucleotide triphosphates (dNTPs). For some applications, the amplified nucleic acid may be fragmented prior to incubation with an oligonoucleotide array, and the extent of hybridization determined by the amount of label now associated with the array. In a preferred embodiment, transcription amplification, as described above, using a labeled nucleotide (e.g. fluorescein-labeled UTP and/or CTP) incorporates a label into the transcribed nucleic acids.

Alternatively, a label may be added directly to the original nucleic acid sample (e.g., mRNA, polyA mRNA, cDNA, etc.) or to the amplification product after the amplification is completed. Such labeling can result in the increased yield of amplification products and reduce the time required for the amplification reaction. Means of attaching labels to nucleic acids include, for example, nick translation or end-labeling (e.g. with a labeled RNA) by kinasing of the nucleic acid and subsequent attachment (ligation) of a nucleic acid linker joining the sample nucleic acid to a label (e.g., a fluorophore).

Detectable labels suitable for use in the present invention include any composition detectable by spectroscopic, photochemical, biochemical, immunochemical, electrical, optical or chemical means. Useful labels in the present invention include biotin for staining with labeled streptavidin conjugate, magnetic beads (e.g., Dynabeads.TM.), fluorescent dyes (e.g., see below and, e.g., Molecular Probes, Eugene, Oreg., USA), radiolabels (e.g., $^{32}$P, $^{33}$P, $^{35}$S, $^{125}$I, and the like), enzymes (e.g., horse radish peroxidase, alkaline phosphatase and others commonly used in an ELISA), and colorimetric labels such as colloidal gold (e.g., gold particles in the 40–80 nm diameter size range scatter green light with high efficiency) or colored glass or plastic (e.g., polystyrene, polypropylene, latex, etc.) beads. Patents teaching the use of such labels include U.S. Pat. Nos. 3,817,837; 3,850,752; 3,939,350; 3,996,345; 4,277,437; 4,275,149; and 4,366,241, which are incorporated in their entirety by reference herein.

Fluorescent moieties or labels of interest include coumarin and its derivatives, e.g. 7-amino-4-methylcoumarin, aminocoumarin, bodipy dyes, such as Bodipy FL, cascade blue, fluorescein and its derivatives, e.g. fluorescein isothiocyanate, Oregon green, rhodamine dyes, e.g. Texas red, tetramethylrhodamine, eosins and erythrosins, cyanine dyes, e.g. Cy3 and Cy5, macrocyclic chelates of lanthanide ions, e.g. quantum dye.TM., fluorescent energy transfer dyes, such as thiazole orange-ethidium heterodimer, TOTAB, etc. As mentioned above, labels may also be members of a signal producing system that act in concert with one or more additional members of the same system to provide a detectable signal. Illustrative of such labels are members of a specific binding pair, such as ligands, e.g. biotin, fluorescein, digoxigenin, antigen, polyvalent cations, chelator groups and the like, where the members specifically bind to additional members of the signal producing system, where the additional members provide a detectable signal either directly or indirectly, e.g. antibody conjugated to a fluorescent moiety or an enzymatic moiety capable of converting a substrate to a chromogenic product, e.g. alkaline phosphatase conjugate antibody; and the like. For each sample of RNA, one can generate labeled oligos with the same labels.

Alternatively, one can use different labels for each physiological source, which provides for additional assay configuration possibilities.

A fluorescent label is preferred because it provides a very strong signal with low background. It is also optically detectable at high resolution and sensitivity through a quick scanning procedure. The nucleic acid samples can all be labeled with a single label, e.g., a single fluorescent label. Alternatively, in another embodiment, different nucleic acid samples can be simultaneously hybridized where each nucleic acid sample has a different label. For instance, one target could have a green fluorescent label and a second target could have a red fluorescent label. The scanning step will distinguish sites of binding of the red label from those binding the green fluorescent label. Each nucleic acid sample (target nucleic acid) can be analyzed independently from one another utilizing the methods of the present invention.

Suitable chromogens which may be employed include those molecules and compounds which absorb light in a distinctive range of wavelengths so that a color can be observed or, alternatively, which emit light when irradiated with radiation of a particular wave length or wave length range, e.g., fluorescers.

A wide variety of suitable dyes are available, being primarily chosen to provide an intense color with minimal absorption by their surroundings. Illustrative dye types include quinoline dyes, triarylmethane dyes, acridine dyes, alizarine dyes, phthaleins, insect dyes, azo dyes, anthraquinoid dyes, cyanine dyes, phenazathionium dyes, and phenazoxonium dyes.

A wide variety of fluorescers may be employed either alone or, alternatively, in conjunction with quencher molecules. Fluorescers of interest fall into a variety of categories having certain primary functionalities. These primary functionalities include 1- and 2-aminonaphthalene, p,p'-diaminostilbenes, pyrenes, quaternary phenanthridine salts, 9-aminoacridines, p,p'-diaminobenzophenone imines, anthracenes, oxacarbocyanine, marocyanine, 3-aminoequilenin, perylene, bisbenzoxazole, bis-p-oxazolyl benzene, 1,2-benzophenazin, retinol, bis-3-aminopyridinium salts, hellebrigenin, tetracycline, sterophenol, benzimidzaolylphenylamine, 2-oxo-3-chromen, indole, xanthen, 7-hydroxycoumarin, phenoxazine, salicylate, strophanthidin, porphyrins, triarylmethanes and flavin. Individual fluorescent compounds which have functionalities for linking or which can be modified to incorporate such functionalities include, e.g., dansyl chloride; fluoresceins such as 3,6-dihydroxy-9-phenylxanthhydrol; rhodamineisothiocyanate; N-phenyl 1-amino-8-sulfonatonaphthalene; N-phenyl 2-amino-6-sulfonatonaphthalene: 4-acetamido-4-isothiocyanato-stilbene-2,2'-disulfonic acid; pyrene-3-sulfonic acid; 2-toluidinonaphthalene-6-sulfonate; N-phenyl, N-methyl 2-aminoaphthalene-6-sulfonate; ethidium bromide; stebrine; auromine-0,2-(9'-anthroyl)palmitate; dansyl phosphatidylethanolamine; N,N'-dioctadecyl oxacarbocyanine; N,N'-dihexyl oxacarbocyanine; merocyanine, 4(3'pyrenyl)butyrate; d-3-aminodesoxy-equilenin; 12-(9'anthroyl)stearate; 2-methylanthracene; 9-vinylanthracene; 2,2'(vinylene-p-phenylene)bisbenzoxazole; p-bis[2-(4-methyl-5-phenyl-oxazolyl)]benzene; 6-dimethylamino-1,2-benzophenazin; retinol; bis(3'-aminopyridinium) 1,10-decandiyl diiodide; sulfonaphthylhydrazone of hellibrienin; chlorotetracycline; N(7-dimethylamino-4-methyl-2-oxo-3-chromenyl)maleimide; N-[p-(2-benzimidazolyl)-phenyl]maleimide; N-(4-fluoranthyl)maleimide; bis(homovanillic acid); resazarin; 4-chloro-7-nitro-2,1,3benzooxadiazole; merocyanine 540; resorufin; rose bengal; and 2,4-diphenyl-3(2H)-furanone.

Fluorescers are generally preferred because by irradiating a fluorescer with light, one can obtain a plurality of emissions. Thus, a single label can provide for a plurality of measurable events.

Detectable signal can also be provided by chemiluminescent and bioluminescent sources. Chemiluminescent sources include a compound which becomes electronically excited by a chemical reaction and can then emit light which serves as the detectible signal or donates energy to a fluorescent acceptor. A diverse number of families of compounds have been found to provide chemiluminescence under a variety or conditions. One family of compounds is 2,3-dihydro-1,-4-phthalazinedione. The must popular compound is luminol, which is the 5-amino compound. Other members of the family include the 5-amino-6,7,8-trimethoxy- and the dimethylamino[ca]benz analog. These compounds can be made to luminesce with alkaline hydrogen peroxide or calcium hypochlorite and base. Another family of compounds is the 2,4,5-triphenylimidazoles, with lophine as the common name for the parent product. Chemiluminescent analogs include para-dimethylamino and -methoxy substituents. Chemiluminescence can also be obtained with oxalates, usually oxalyl active esters, e.g., p-nitrophenyl and a peroxide, e.g., hydrogen peroxide, under basic conditions. Alternatively, luciferins can be used in conjunction with luciferase or lucigenins to provide bioluminescence.

Spin labels are provided by reporter molecules with an unpaired electron spin which can be detected by electron spin resonance (ESR) spectroscopy. Exemplary spin labels include organic free radicals, transitional metal complexes, particularly vanadium, copper, iron, and manganese, and the like. Exemplary spin labels include nitroxide free radicals.

A label may be added to the target (sample) nucleic acid(s) prior to, or after the hybridization. So called "direct labels" are detectable labels that are directly attached to or incorporated into the target (sample) nucleic acid prior to hybridization. In contrast, so called "indirect labels" are joined to the hybrid duplex after hybridization. Often, the indirect label is attached to a binding moiety that has been attached to the target nucleic acid prior to the hybridization. Thus, for example, the target nucleic acid may be biotinylated before the hybridization. After hybridization, an avidin-conjugated fluorophore will bind the biotin bearing hybrid duplexes providing a label that is easily detected. For a detailed review of methods of labeling nucleic acids and detecting labeled hybridized nucleic acids see Laboratory Techniques in Biochemistry and Molecular Biology, Vol. 24: Hybridization With Nucleic Acid Probes, P. Tijssen, ed. Elsevier, N.Y., (1993)).

Fluorescent labels are preferred and easily added during an in vitro transcription reaction. In a preferred embodiment, fluorescein labeled UTP and CTP are incorporated into the RNA produced in an in vitro transcription reaction as described above.

The labels may be attached directly or through a linker moiety. In general, the site of label or linker-label attachment is not limited to any specific position. For example, a label may be attached to a nucleoside, nucleotide, or analogue thereof at any position that does not interfere with detection or hybridization as desired. For example, certain Label-ON Reagents from Clontech (Palo Alto, Calif.) provide for labeling interspersed throughout the phosphate backbone of an oligonucleotide and for terminal labeling at the 3' and 5' ends. For example, labels may be attached at positions on the ribose ring or the ribose can be modified and even eliminated as desired. The base moieties of useful labeling reagents can include those that are naturally occurring or modified in a manner that does not interfere with their function. Modified bases include but are not limited to 7-deaza A and G, 7-deaza-8-aza A and G, and other heterocyclic moieties.

One of skill in the art would appreciate that many of the detectable labels described above for nucleic acid sequences may be readily incorporated into polypeptides. The labels may be attached directly or through a linker moiety. In general, the site of label or linker-label attachment is not limited to any specific position. For example, a label may be attached to an amino acid or analogue thereof at any position that does not interfere with detection or interaction as desired. Alternatively, interactions involving polypeptides (e.g., nucleic acid-protein or protein-protein binding) may be visualized using "indirect labels", which are joined to the specific binding pair after the formation of a complex. The indirect label may be attached to a binding moiety that has been linked to the target polypeptide prior to the binding interaction. Thus, for example, the target polypeptide may be biotinylated before the binding interaction. After binding, an avidin-conjugated fluorophore will bind the biotin bearing specific binding pair providing a label that is easily detected.

Microarray Analysis

Figure 1:
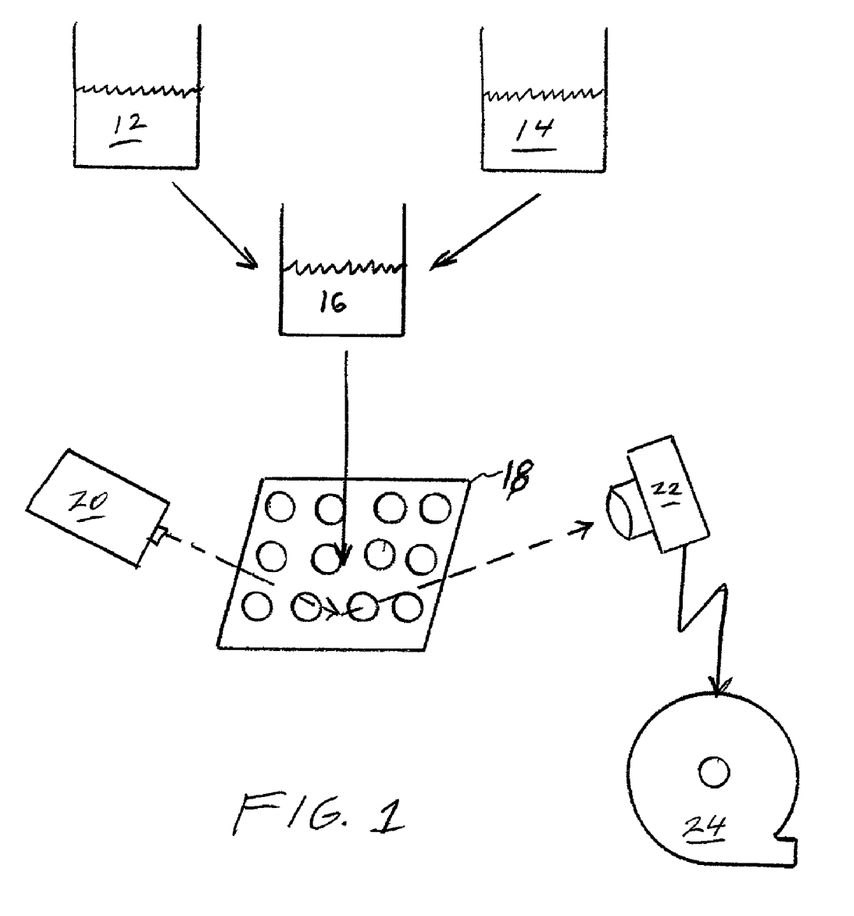
FIG. 1 is a diagram of apparatus and a method of obtaining fluorescence image data from a genetic microarray.

Referring to FIG. 1, there is shown a diagram by which a DNA microarray is prepared for analysis. Two heterogeneous samples 12 and 14 containing mRNA sequences are provided. To the first sample 12, a quantity of Cy3 marker is added to bind with the mRNA therein. To the second sample 14, a quantity of Cy5 marker is added to bind with the mRNA therein. The two samples are then mixed to provide a heterogeneous sample 16 and applied to the DNA microarray 18.

The microarray 18 is then excited by irradiation with a scanning laser 20, and the resulting image is captured digitally, such as by a CCD (charge-coupled device) image sensor 22. The resulting digital image is then stored in a standard format, such as a 16-bit TIFF (tagged image file format) file 24. The digital image file 24 consists of an array of intensity data corresponding the detected image intensities.

Figure 2:
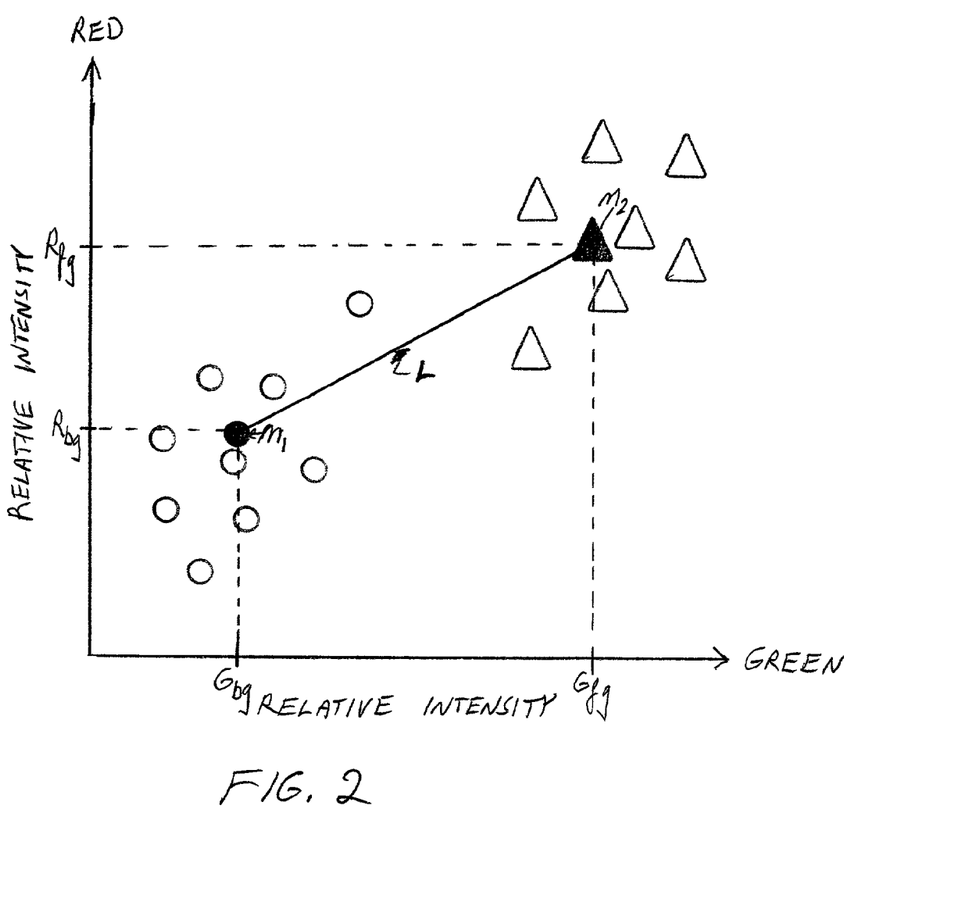
FIG. 2 is a graph of fluorescence image data arranged by red and green intensity coordinates and illustrating the analysis technique of the invention.

In accordance with the present method, the image data is analyzed as two clusters in R-G intensity space, as shown in FIG. 2. Each image pixel, having respective red and green intensity values R and G, is represented as points $(R_i, G_i)$ in R-G space (shown in FIG. 2 collectively as open circles and open triangles). A clustering analysis technique is applied in order to (a) divide the (R, G) values into a respective background cluster (shown by open circles) and a foreground cluster (shown by open triangles) and to (b) determine representative points $(R_{bg}, G_{bg})$ and $(R_{fg}, G_{fg})$, such as medoids $m_1$ and $m_2$, which characterize each cluster. The intensity ratio is then determined on the basis of these two points and is provided as a measure of the relative marker abundance at each gene spot. Two such clustering techniques will now be described.

I. Partitioning Around Medoids (PAM)

The PAM technique is adapted from KAUFMAN, L. and ROUSSEEUW, P. J. (1990) *Finding groups in data: An introduction to cluster analysis*, Wiley, New York.

In the PAM technique, medoid locations among a set of k clusters are determined by minimization of an objective function:

$$\sum_{i=1}^{n} \min_{k=1\ldots K} d(x_i, m_k)$$

where $d(x_i, m_k)$ is the distance between the ith pixel of a cluster and a tentatively proposed medoid $m_k$. The medoid value is determined iteratively by testing successive $m_k$ values until the k local minima of the function are obtained. For application to the problem of obtaining foreground and background clusters of R and G intensity values of a probe region of a DNA microarray, k is equal to 2.

Figure 3:
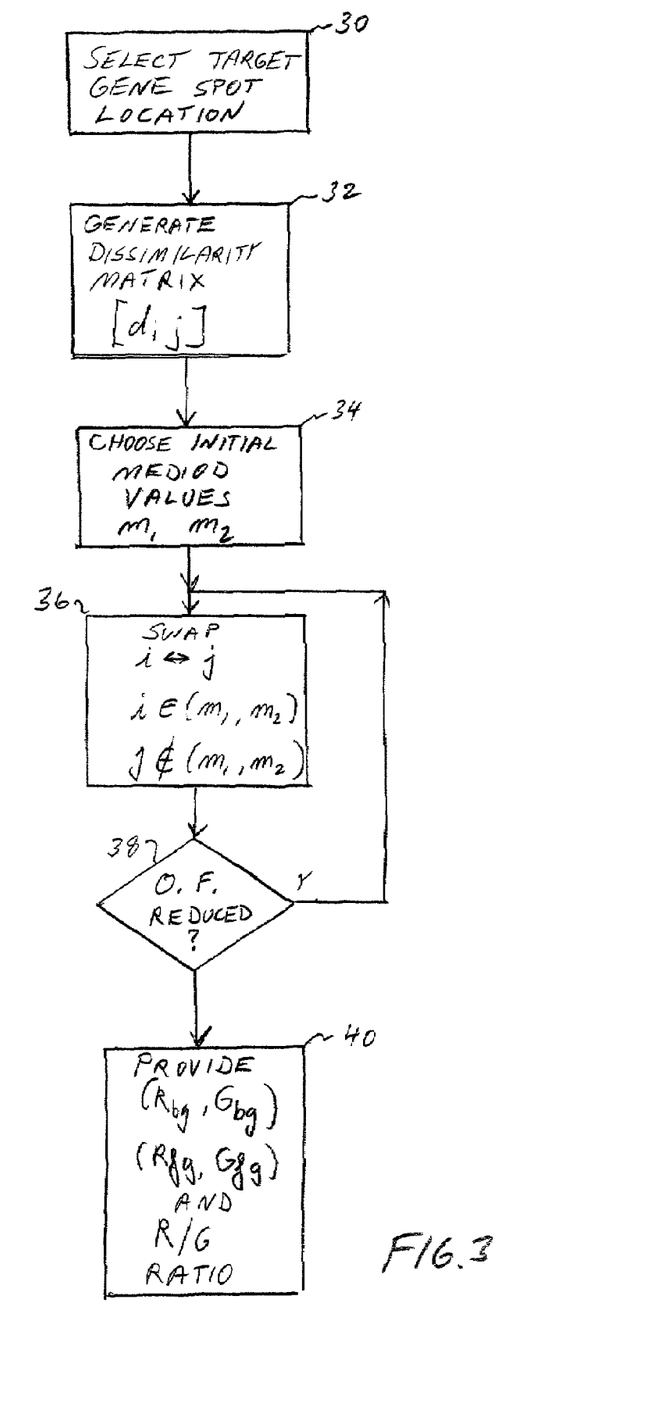
FIG. 3 is a logical flow diagram of a first analysis method of the invention.

Referring now to FIG. 3, there is shown a flow diagram of a first analysis method of the invention. Beginning at step 30, a first target location is chosen. The first target location may be a subset of the TIFF image data corresponding to a predetermined array of pixels about the first probe location on the DNA microarray. Such a location may be, for example, a 30×30 pixel region.

In step 32, a dissimilarity matrix of spot pixels is calculated as follows. The manhattan distances between all pairs of pixels is calculated. The distance function $d_{ij}$ between the intensity values of pixels $x_i$ and $x_j$ (having values of $(R_i, G_i)$ and $(R_j, G_j)$ is the sum of the absolute distances:

$$d_{ij} = d(x_i, x_j) = |R_i - R_j| + |G_i - G_j|$$

The medoids of the clusters in R-G space are determined iteratively. In step 34, two initial medoids $m_1$ and $m_2$ are chosen. The first initial medoid, $m_1$ is selected as the object which the smallest value of:

$$\sum_{i=i}^{n} d(x_i, m_1)$$

The second initial medoid, $m_2$, is selected as the object which minimizes the objective function with the fixed value of $m_1$.

Once the initial medoid values have been chosen, a swap phase of the process is begun in step 36. In this step, the following procedure is repeated until convergence at stable values is reached. For all objects (i, j), where:

$i \in (m_1, m_2)$ and where:

$j \notin (m_1, m_2)$ the values of i and j are swapped and the objective function is recalculated. In step 38, if the present value of the objective function is reduced, then the swap is maintained and step 36 is repeated. Swaps are performed until no further reduction in the objective function occurs. The resulting vectors $m_1$ and $m_2$ are the final medoids, and the method proceeds to step 40.

Finally, in step 40 the intensity values of the final medoid pixel having the lowest intensity values is determined to be the background medoid $(R_{bg}, G_{bg})$ and the other medoid pixel is determined to be the foreground medoid $(R_{fg}, G_{fg})$. The relative abundance ratio is determined as the ratio of the difference in intensities of the respective red and green intensity values of the medoid pixels.

$$R/G = \frac{R_{fg} - R_{bg}}{G_{fg} - G_{bg}}$$

The intensity ratio may be visualized as the slope of the line L joining the medoid pixels in R-G intensity space, as shown in FIG. 2.

II. K-means Method

An alternative clustering method which may be applied to genetic microarray image data is a K-means method of the type described in [MACQUEEN (1967): Some methods for classification and analysis of multivariate observations, Proc. 5th Berkeley Symposium on Math. Stat. and Prob.]. This method is described in conjunction with FIG. 4.

Figure 4:
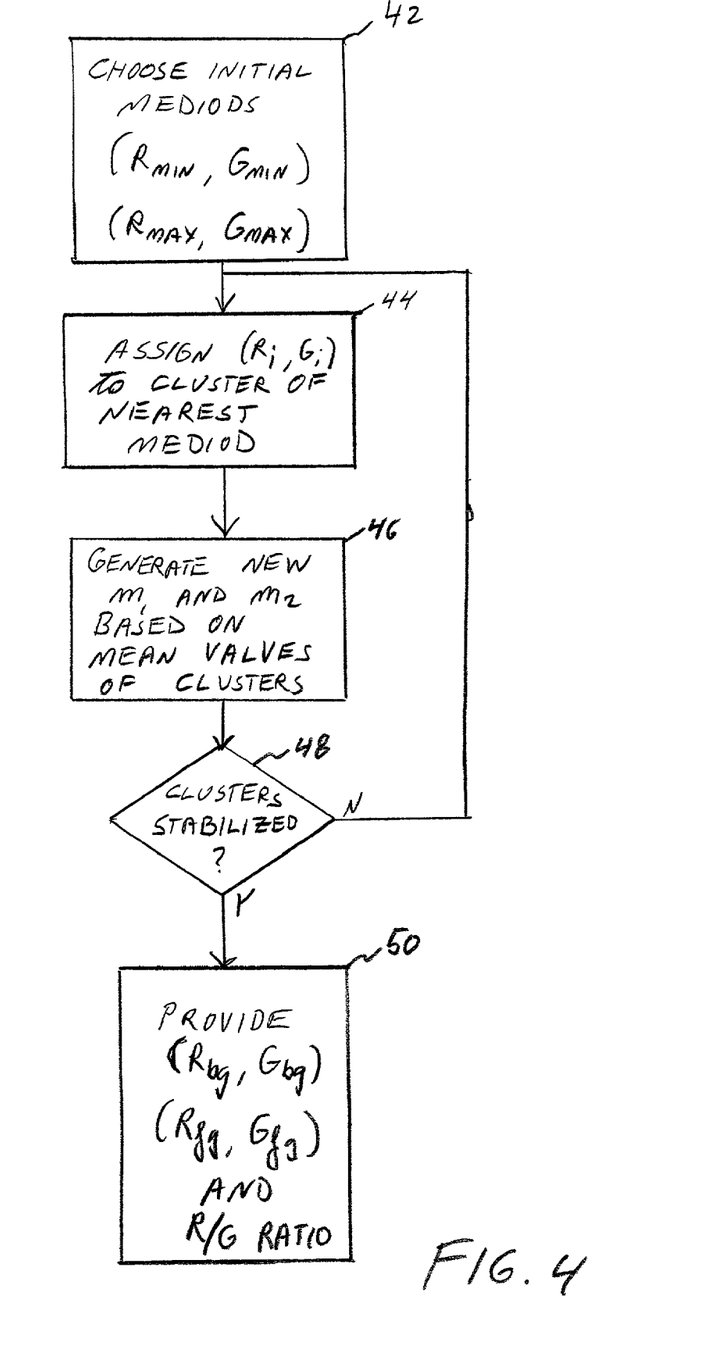
FIG. 4 is a logical flow diagram of a second analysis method of the invention.

A target spot is chosen, as before. Then, beginning at step 42, initial representative pixels are chosen as initial candidate pixels, or prototypes. Such prototypes may be $m_1 = (R_{fg}, G_{fg})$ and $m_2 = (R_{bg}, G_{bg})$, where the respective R,G values are R,G values of the pixels having the highest and lowest intensity values.

In step 44, a local optimization is begun as follows. Each data point in the image is assigned to a cluster of the closest prototypes $m_1$ or $m_2$. Then, in step 46 within each cluster two new prototypes are chosen as the coordinates of the arithmetic mean of all data points assigned to each cluster. This step is repeated until it is determined in step 48 that convergence has been reached based on stable cluster assignments for all pixels.

Finally, in step 50, the convergence values of $m_1$ and $m_2$ are determined to be the medoid values in R-G space for the background and foreground medoids as before, and the intensity ratio is calculated in the same manner.

In further alternative embodiments, the arithmetic mean in step 46 may be replaced by another statistical measure, such as a median value, in order to encounter outliers. In general method II presents less computational complexity relative to method I. In rare cases, the gene spot itself may be of lower intensity than the surrounding background area, which would lead to an inadvertent swapping of the actual foreground and background intensities determined for the spot. In order to detect such cases, spots for which the spatial dispersion in actual coordinate space of the determined foreground area is greater than that of the background area can be implemented as a check step prior to determination of the R/G ratio for that spot.

The pixel clustering methods described above may be conducted in parallel with other methods of gene spot image analysis, such that these methods are combined with other methods to produce multiple results which can then be weighted or otherwise combined together in dependence on a confidence criterion.

A visual confirmation of the clustering method may be obtained by producing a bivalence plot of a gene spot under consideration. Once each pixel in the image has been determined to belong to either a foreground cluster or a background cluster, a monochromatic bivalence image of the spot is formed by assigning, for example, a white value to foreground pixels and a black value to background pixels. Correspondence between the bivalence plot and the visual appearance of the full color image provides a visual check on the accuracy of the clustering analysis. Additionally, the clustering method can be repeated for the subset of all image pixels falling within the foreground region of the bivalence plot, to further eliminate the influence of outlier pixels in the background region.

While certain of the preferred embodiments of the present invention have been described and specifically exemplified above, it is not intended that the invention be limited to such embodiments. Various modifications may be made thereto without departing from the scope and spirit of the present invention, as set forth in the following claims.

What is claimed is:

1. A method of determining the relative abundance of genetic material present in a first sample and a second sample, comprising the steps of:
   labeling the first sample with a first detectable label adapted to bind with genetic material therein;
   labeling the second sample with a second detectable label adapted to bind with genetic material therein;
   providing a substrate with a binding area thereon for hybridizing with a genetic sequence;
   contacting the substrate comprising said genetic sequence with the first and second samples under conditions suitable to effect hybridization;
   obtaining a digital image of the binding area under conditions causing said labels to manifest an image intensity dependent on the abundance of genetic material bound to the binding area, if any, thus providing an array of pixel values comprising respective intensity values corresponding the first and second labels;
   assigning each of said pixel values to a respective one of a foreground cluster and a background cluster;
   determining a representative statistical vector of pixel values within each of said foreground cluster and said background cluster; and
   computing the relative abundance of genetic material within the first and second samples corresponding to the binding area in proportion to a ratio of differences between the respective coordinates of the representative statistical vectors.

2. The method of claim 1 wherein said representative statistical vectors are a pair of medoid vectors for the respective clusters, and wherein said respective clusters comprise a foreground cluster and a background cluster.

3. The method of claim 2 wherein said determining step is one of a Partition Around Medoids analysis step and a K-Means analysis step.

4. The method of claim 3, further comprising the steps of:
   generating a bivalent mask of the respective background and foreground areas of the binding area based on the outcome of said clustering procedure; and
   re-applying said clustering procedure to pixels located within a determined foreground cluster, prior to providing said measure of abundance.

5. The method of claim 3, further comprising the steps of:
   calculating the spatial dispersion of image pixels corresponding to said determined foreground cluster;
   calculating the spatial dispersion of image pixels corresponding to said determined background cluster; and
   reversing the determination of foreground and background clusters if the spatial dispersion of said determined foreground cluster exceeds the spatial dispersion of said background cluster.

6. The method of claim 3, further comprising the steps of:
   generating a bivalent mask of the respective background and foreground areas of the binding area based on the outcome of said clustering procedure; and
   generating a display of said bivalent mask for visual comparison with the image of the binding area.

* * * * *